United States Patent

Gaillard-Kelly et al.

Patent Number: 5,084,450
Date of Patent: Jan. 28, 1992

[54] NOVEL STEROIDS

[75] Inventors: Martine Gaillard-Kelly, Paris; Lucien Nedelec, Le Raincy; Francois Nique, Pavillons sous Bois; Daniel Philibert, La Varenne Saint Hilaire, all of France

[73] Assignee: Roussel Uclaf, France

[21] Appl. No.: 658,003

[22] Filed: Feb. 20, 1991

[30] Foreign Application Priority Data

Feb. 22, 1990 [FR] France .................. 90 02177

[51] Int. Cl.[5] .................. A61K 31/56; C07C 11/00
[52] U.S. Cl. .................. 514/177; 552/508; 514/182
[58] Field of Search .................. 514/177, 178; 552/508

[56] References Cited

U.S. PATENT DOCUMENTS 4,474,702 10/1984 Karanewsky et al. .............. 552/508

Primary Examiner—Howard T. Mars
Assistant Examiner—Kimberly J. Kestler
Attorney, Agent, or Firm—Bierman and Muserlian

[57] ABSTRACT

Compounds of the formula

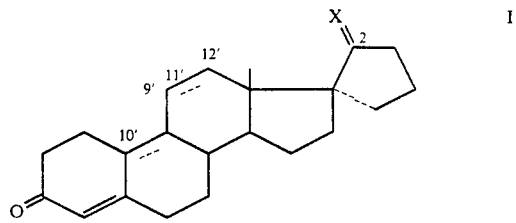

wherein $=X$ is $=O$ or $$\begin{matrix} \sim OR \\ \sim H \end{matrix},$$

R is hydrogen or acyl of an organic carboxylic acid of 1 to 12 carbon atoms, the wavy lines indicate the α- or β-position, the dotted line in the 17-position indicates the bond is in the α-position and the dotted lines in the 9'(10') and 11'(12') positions indicate an optional double bond in the 9'(10') position or two optional double bonds in the 9'(10') and 11'(12') positions having progestomimetic and antiestrogenic activity.

10 Claims, No Drawings

NOVEL STEROIDS

STATE OF THE ART

Related prior art includes U.S. Pat. No. 3,968,132.

OBJECTS OF THE INVENTION

It is an object of the invention to provide the novel compounds of formula I and a novel process and intermediates for their preparation.

It is another object of the invention to provide novel progestomimetic compositions and a method of inducing progestomimetic activity warm-blooded animals.

These and other objects and advantages of the invention will become obvious from the following detailed description.

THE INVENTION

The novel steroids of the invention are compounds of the formula

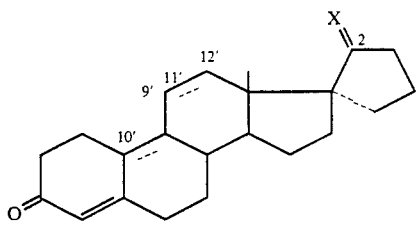

wherein =X is =O or

OR
H

R is hydrogen or acyl of an organic carboxylic acid of 1 to 12 carbon atoms, the wavy lines indicate the α- or β-position, the dotted line in the 17-position indicates the bond is in the α-position and the dotted lines in the 9'(10') and 11'(12') positions indicate an optional double bond in the 9'(10') position or two optional double bonds in the 9'(10') and 11'(12') positions.

Examples of acyl of an organic carboxylic acid of 1 to 12 carbon atoms are acetyl, propionyl and benzoyl.

Due to the presence of an asymmetrical carbon on the spiro ring in position 2 when =X is

OH
H two epimers can exist, namely (2R or 2S) as well as thereof.

The products can be 3'-keto-Δ4'-products when the two dotted lines in positions 9'(10') and 11'(12') are not a double bond between the carbons which carry them. The invention also relates to 3'-keto-Δ4',9'(10')-products and the 3'-keto-Δ4',9'(10'), 11'(12')-trienones.

Among the preferred products of formula I are those wherein X is oxygen and the dotted line in position 11'(12') does not indicate the presence of a second bond between the carbons which carry it. A preferred compound is spiro (cyclopentane-1,17'β -Δ4,9-estradiene)-2,3'-dione.

The novel process for the preparation of the compounds of formula I comprises subjecting a compound of the formula

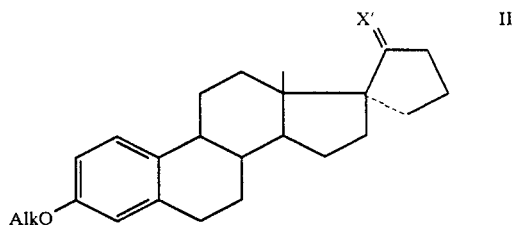

wherein =X' is an optionally protected ketone or

OH
H

R has the above-indicated definition, in the form of each of the epimers 2R or 2S in the form of a mixture of these epimers and Alk is alkyl of 1 to 4 carbon atoms with either to a reduction followed by hydrolysis to obtain a compound of the formula

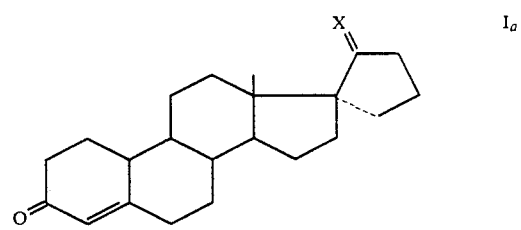

wherein X has the above definition and corresponding to the products of formula I in which the dotted lines in position 9'(10') and 11'(12') are not a second bond between the carbons which carry them, or to a reduction followed by a gentle hydrolysis, then by a dehydrogenation to obtain a compound of the formula

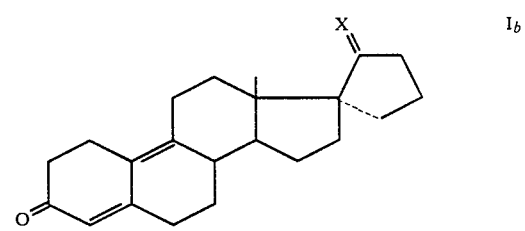

corresponding to the products of formula I in which the dotted lines in position 9'(10') indicate the presence of a double bond and those in position 11'(12') do not represent a double bond and the products of formula I$_b$ are optionally subjected to a protection reaction in position 3, followed by a gentle hydrolysis, then by a dehydrogenation to obtain a compound of the formula

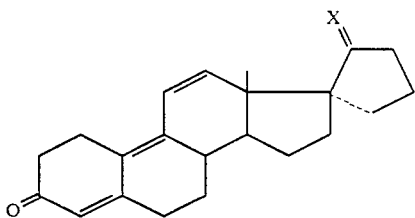

corresponding to the products of formula I in which the dotted lines in positions 9'(10') and 11'(12') indicate the presence of two additional double bonds in position 9'(10') and 11'(12'), and optionally the products of formulae $I_a$, $I_b$ and $I_c$ in which =X is

are subjected either to an oxidation reaction to obtain the corresponding products of formulae $I_a$, $I_b$ and $I_c$ in which X is oxygen, or to an acylation reaction to obtain the products in which =X is

in which R is acyl.

When X' is a protected ketone, it is preferably a (cyclic or non-cyclic ketal) such as dimethyl- and diethylketal or ethylenedioxy. Examples of alkyl of Alk in the product of formula II are methyl, ethyl, linear or branched propyl, linear or branched butyl, with methyl being preferred.

The reduction of the products of formula II to obtain the products of formula $I_a$ is preferably the so-called BIRCH reaction carried out using lithium in liquid ammonia in the presence of an alcohol such as methanol, ethanol or tert-butanol. The hydrolysis is preferably carried out using a strong acid such as hydrochloric acid, p-toluene sulfonic acid or oxalic acid preferably in a solvent such as methanol. This hydrolysis normally allows X' to be converted into the ketone when it is a protected ketone.

The preparation of the products of formula $I_b$ is carried out first using a BIRCH reduction as set out above and the gentle hydrolysis is then carried out using a weak acid such as acetic acid or propionic acid. The final dehydrogenation is carried out preferably by the so-called bromination-debromhydration method. The bromination is undertaken preferably using pyridinium perbromide and the debromhydration is effected with a base such as pyridine or triethylamine. The two reactions can be carried out simultaneously by using the mixture pyridinium perbromide-pyridine.

During the optional conversion of the products of formula $I_b$ into the products of formula $I_c$, the protection of the 3-ketone is carried out as indicated for X'. The gentle hydrolysis is then carried out as indicated above. The final dehydrogenation preferably uses chloranile or dichlorodicyanobenzoquinone (DDQ).

The optional oxidation of the products of formulae $I_a$, $I_b$ and $I_c$ in which =X is

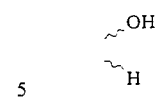

is carried out preferably using standard reagents such as chromic acid in acetone (Jones reagent), aluminium isopropylate in the presence of cyclohexanone (Oppenauer reagent) or pyridinium chlorochromate. When, in the products of formula II, $I_a$ $I_b$, and $I_c$, =X' or =X is

the mixture of epimers can be separated into each of its epimers by standard methods such as chromatography on a silica column.

The optional esterification of the alcohol is carried out preferably using a reactive derivative of the acyl such as an acid halide, preferably an acid chloride, a mixed or symmetrical anhydride or using the carboxylic acid corresponding to the acyl using a dehydration agent such as dicyclohexyl carbodiimide (DCC).

The process for the preparation of the compounds of formula I' wherein =X is

R having the above meaning comprises reacting a compound of the formula

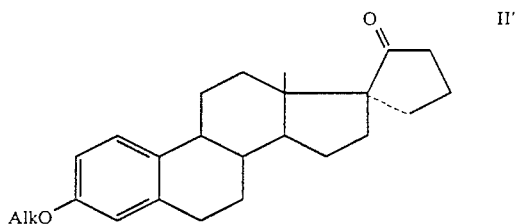

with a reduction reagent to obtain a compound of the formula

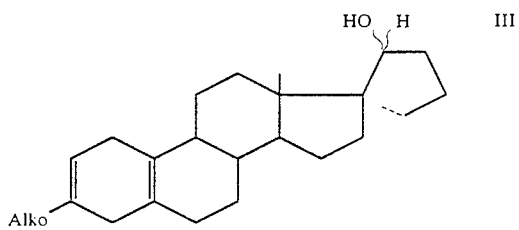

which is separated optionally into each of its isomers and the products of formula III in the form of an epimer mixture or in the form of pure products, are subjected either to a hydrolysis to obtain a compound of the formula

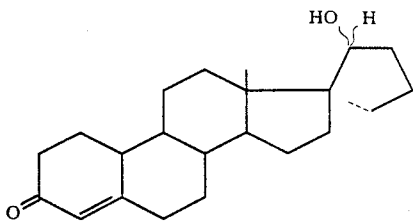

which products are optionally separated into each of their isomers, or to a gentle hydrolysis followed by a dehydrogenation to obtain a compound of the formula

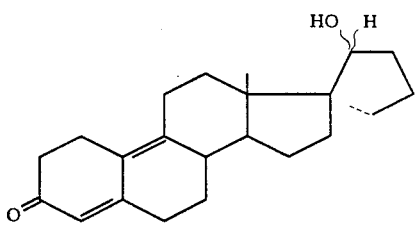

which are optionally separated into each of their isomers and the products of formula I′$_b$ in the form of an epimer or in the form of pure products are optionally subjected to a protection reaction in 3-position followed by a gentle hydrolysis then by a dehydrogenation to obtain a compound of the formula

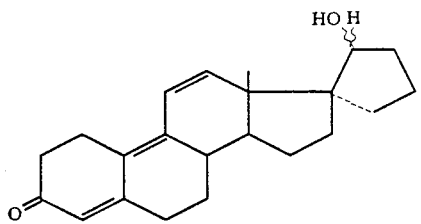

which are optionally separated into each of their isomers and optionally the products of formulae I′$_a$, I′$_b$ and I′$_c$ or if appropriate their isomers are subjected to an acylation to obtain the corresponding products in which =X is

in which R is acyl.

The reduction reaction to which the products of formula II′ are subjected to obtain the products of formula III is preferably a BIRCH reaction carried out under the above conditions.

The hydrolysis of the products of formula III to obtain the products of formula I′$_a$ is a hydrolysis preferably carried out with a strong acid such as those indicated above.

The gentle hydrolysis, then the dehydrogenation of the products of formula III to obtain the products of formula I′$_b$ are on the one hand a hydrolysis using a weak acid and on the other hand a bromination debromhydration such as those indicated above for the preparation of the process of formula I$_b$.

The protection in 3-position, then the gentle hydrolysis and finally the dehydrogenation of the products of formula I′$_b$ to obtain the products of formula I′$_c$ are carried out under the same conditions as indicated above for the conversion of the products of formula I$_b$ into the products of formula I$_c$. The optional separation of the isomer mixtures is carried out by standard methods such as chromatography.

During the conversion of the products of formula I$_b$ into the products of formula I$_c$, the products of formula IV are obtained intermediately:

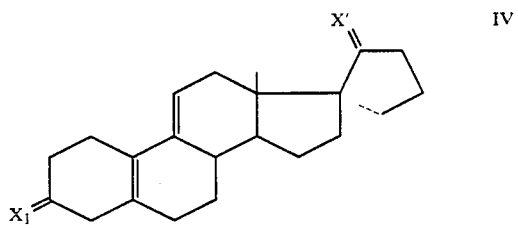

which X′ has the above meaning and X$_1$ is a protected ketone.

The novel progestomimetic and antiestrogenic compositions of the invention are comprised of an effective amount of at least one compound of formula I and an inert pharmaceutical carrier or excipient. The compositions may be in the form of tablets, dragees, cachets, capsules, granules, emulsions, syrups, suppositories, injectable solutions and suspensions, ointments, creams, gels, patches and aerosol compositions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, the various wetting, dispersing and emulsifying agents and preservatives.

The compositions are useful as progestative compositions useful as hypophysiary inhibitors of anti-LH predominance or as antiestrogens. They are useful in the treatment of dysmenorrhea, sterility, ovarian dystrophies by resting the ovaries, in the treatment of breast and uterine tumors, and as contraceptives. The compositions are also useful in the hormonal treatment of the menopause and osteoporosis.

The novel method of inducing progestomimetic and anti-estrogenic activity in warm-blooded animals, including humans, comprises administering to warm-blooded animals an effective amount of at least one compound of formula I. The compounds may be administered orally, rectally, parenterally or topically to the skin or mucous membranes. The usual daily dose is 1.33 to 133.3 μg/kg depending on the condition treated, the specific compound and method of administration.

The products of formula II are new products and may be prepared by reacting lithium in liquid ammonia with a compound of the formula

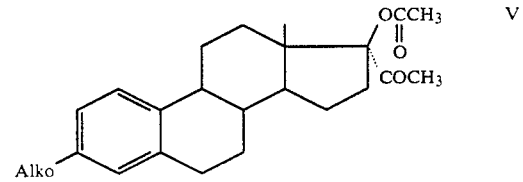

in which Alk has the above meaning and, then with a product of the formula

Hal—CH$_2$—CH=CH$_2$  VI in which Hal is halogen to obtain a compound of the formula

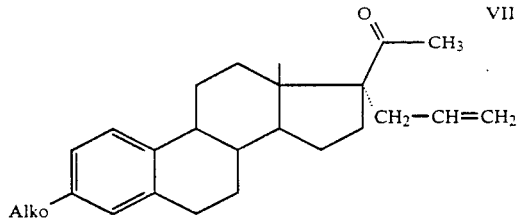
VII and subjecting the latter to an ozonolysis to obtain a compound of the formula

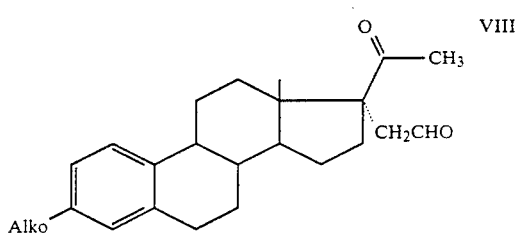
VIII treating the latter with a base to obtain a compound of the formula

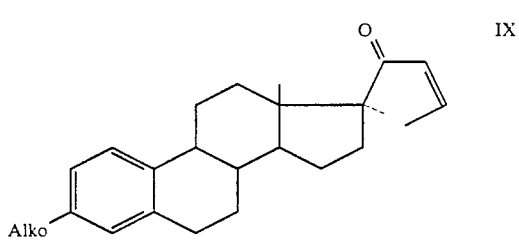
IX subjecting the latter to a hydrogenation to obtain a compound of

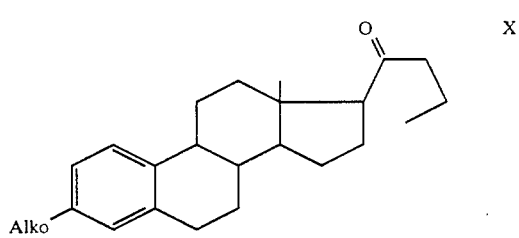
X and subjecting the latter either to a protection reaction of the ketone to obtain the products of formula II in which X' is a protected ketone or to a reduction reaction followed optionally by a separation of the isomers to obtain the products of formula II in which X' is a protected ketone, or to a reduction reaction followed optionally by a separation of the isomers to obtain the products of formula II in which =X' is

The said products can be subjected to an acylation reaction to obtain the products of formula II in which =X' is

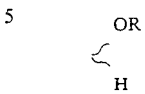

in which R is acyl. The halogen that is Hal is preferably bromine. The base with which the products of formula VIII are treated to obtain the products of formula IX is preferably potassium hydroxide in methanol.

The hydrogenation of the products of formula IX to obtain the products of formula X is preferably carried out with hydrogen in the presence of a catalyst such as palladium on activated charcoal, preferably in a solvent such as tetrahydrofuran.

The optional protection of the ketone is carried out in the usual conditions such as with ethylene glycol in the presence of p-toluene sulfonic acid to prepare the cyclic ketal. The optional reduction of the products of formula X is carried out preferably in the presence of a hydride such as lithium aluminium hydride or sodium borohydride. The optional acylation is carried out under the conditions indicated above.

The products of formula V are described in U.S. Pat. Nos. 3,062,845 and No. 3,775,443. The products in which Alk is methyl are preferred.

In the following examples, there are described several preferred embodiments to illustrate the invention. However, it should be understood that the invention is not intended to be limited to the specific embodiments.

EXAMPLE 1

Spiro (cyclopentane-1,17′β-Δ4′-estrene)-2,3′-dione

STEP A: 3′-methoxy-spiro (cyclopentane-1,17′β-Δ$^{1',3',5'(10')}$-estratrien)-2-one cyclic (1,2-ethanediyl)-acetal 9 ml of ethyl orthoformate and 90 mg of p-toluene sulfonic acid were added to a solution of 4.5 g of 3′-methoxy-spiro (cyclopentane-1,17′β-Δ$^{1',}$ 3′, 5′(10′)-estratrien)-2-one in 18 ml of chloroform and 18 ml of ethyleneglycol and the mixture was refluxed for one hour. The mixture was cooled, alkalinized with a few ml of triethylamine and then poured into an aqueous saturated solution of sodium bicarbonate. After extraction with ethyl acetate, the extracts were washed with salt water, dried over magnesium sulfate and the solvent was evaporated to obtain 6.36 g of colored crystals which were crystallized from the smallest amount of isopropyl ether by heating and cooling. After drying, 4 g of the expected product melting at 117° C. to 118° C. were obtained. 500 mg of this product were crystallized from isopropyl ether to obtain 375 mg of white crystals melting at 118° C. to 119° C. and having a specific rotation of [α]$_D$= +26°±1.5° (c=0.95% in CHCl$_3$).

Analysis: C$_{25}$H$_{34}$O$_3$; molecular weight=382.55
Calculated: %C 78.49; %H 8.96;
Found: 78.8; 9.1;

STEP B: Spiro (cyclopentane-1,17′β-Δ$^{4'}$-estrene)-2,3′-dione 3 g of the product of Step A in solution in 4 ml of ethanol and 60 ml of anhydrous tetrahydrofuran were added to 36 ml of ammonia condensed to −40° C. to −50° C. and then 540 mg of lithium were added. 250 mg of lithium and 2 ml of ethanol were then added. After the reaction had finished, the ammonia was distilled off and the mixture was diluted with water and extracted with ethyl acetate. The gummy residue was taken up in ether and the solution was filtered. After evaporation of the solvent, 3.06 g of product were obtained which were dissolved in a mixture of 60 ml of ethanol, 10 ml of methylene chloride and 10 ml of 2N hydrochloric acid. The mixture stood for one hour at ambient temperature and then 10 ml of 2N hydrochloric acid were added and the mixture was heated for 40 minutes at 55° C. After cooling and diluting with water, extraction was done with methylene chloride. The extracts were washed with water, dried and evaporated to obtain 3 g of crystallized residue which was chromatographed on silica (eluant: cyclohexane - ethyl acetate (7-3)) to obtain 2 g of product. After crystallization from a methylene chloride isopropyl ether mixture, 1.96 g of the expected product melting at 172° C. were obtained.

| Infra-red (CHCl$_3$) | |
| --- | --- |
| 1721 cm$^{-1}$ | cyclopentanone |
| 1633-1618 cm$^{-1}$ | dienone |

Ultra-violet (ethanol)
Maximum at 239 nm epsilon=18100;
Maximum at 304 nm

PREPARATION: 3'-methoxy-spiro (cyclopentane-1,17'β-Δ$^{1,3,5(10)}$-estra-trien)-2-one used at the start of Example 1 was obtained as follows:

STEP 1:
17α-allyl-3methoxy-19nor-Δ$^{1,3,5(10)}$-pregnatrien-20-one 1.1 g of lithium were added to 500 ml of condensed ammonia and then 25.9 g of 17β-acetoxy-3-methoxy-19-nor-17α-Δ1,3,5(10)-pregnatrien-20-one in solution in 120 ml of anhydrous tetrahydrofuran were added dropwise. The ammonia was distilled off under an inert atmosphere and 25 ml of allyl bromide were added at 20° C. 30 ml of anhydrous tetrahydrofuran were added and the mixture was stirred for 16 hours at ambient temperature. The mixture was diluted with water and extracted with ethyl acetate. The extracts were washed with water, dried and distilled under reduced pressure to obtain 24 g of product. Crystallization was carried out from a methylene chloride - ethanol mixture, followed by ice- cooling, washing with ethanol and drying at 60° C. under reduced pressure to obtain 13.78 g of the expected product melting at 110° C. The mother liquors were evaporated to dryness under reduced pressure and the residue was taken up in cyclohexane under reflux, and a partial dissolution was obtained. The soluble phase was chromatographed on silica (eluant: methylene chloride - cyclohexane (95-5)). Another 1.5 g of expected product was collected, an analytical sample of which was obtained by crystallization from aqueous methanol, pentane - cyclohexane and finally ethanol to obtain the expected product melting at 126° C.

| Infra-red (CHCl$_3$) | |
| --- | --- |
| 1696 cm$^{-1}$ | CO in position 20 |
| 1357 cm$^{-1}$ | CH$_3$ |
| 991, 922 and 1642 cm$^{-1}$ | —CH=CH$_2$ |

Ultra-violet (CHCl$_3$-EtOH)
273 nm: inflexion,
279 nm: maximum epsilon=2000,
286 nm: maximum epsilon=1900, STEP 2:
3-methoxy-20-oxo-19-nor-Δ$^{1,3,5(10)}$-pregnatrien-17α-acetaldehyde Ozonic oxygen was bubbled through a solution of 1 g of the product of Step 1 in 30 ml of methylene chloride cooled to −65° C. to −70° C. until the initial compound had disappeared. Degassing was carried out with a current of argon and a mixture of 2.5 g of powdered zinc, 5 ml of acetic acid and 10 ml of water was added. The mixture was stirred at ambient temperature for 17 hours and the precipitate was separated out, washed with water and then with a solution of sodium bicarbonate. After drying and evaporating, 1 g of the expected product was obtained. Chromatography was carried out on silica with a benzene - ethyl acetate mixture (95-5) to obtain 740 mg of the expected product. By successive crystallizations from a methylene chloride - isopropyl ether mixture, then from aqueous tetrahydrofuran, pure crystals were obtained melting at 138° C.
Infra-red (CHCl$_3$):
Absence of —HC=CH$_2$.
1724 cm$^{-1}$: C=0 aldehyde,
1688 cm$^{-1}$: CO in position 20,
1501, 1577 and 1610 cm$^{-1}$: aromatic.

STEP 3 : 3'-methoxy-spiro (cyclopent-3-en-1,17'β-Δ$^{1',3'5'(10)}$-estratrien)-2-one 5 ml of methylene chloride were added to a mixture of 734 mg of the product of Step 2 in 15 ml of 0.5N methanolic potassium hydroxide and after one hour at ambient temperature, the mixture was diluted with water and extracted with methylene chloride. The extracts were washed, dried and evaporated under reduced pressure to obtain 700 mg of the expected product. After chromatography on silica, 600 mg of purified product were obtained, which was crystallized successively from methylene chloride - isopropyl ether, then methylene chloride - methanol mixtures to obtain the expected product melting at 148° C.
Infra-red (CHCl$_3$):
1691 cm$^{-1}$ : conjugated ketone,
1610 cm$^{-1}$ : C=C
1595, 1575, 1499 cm$^{-1}$: aromatic.

STEP 4: 3'-methoxy-spiro (cyclopentane-1,17'β-Δ$^{1',3'5'(10)}$-estratrien)-2-one 5 g of the product of Step 3 dissolved in 50 ml of tetrahydrofuran were hydrogenated in the presence of 100 mg of 10% palladium on activated charcoal and under a pressure of 1300 mBars of hydrogen. After one hour of stirring, the solution was filtered and evaporated to obtain 5.1 g of the expected product which was crystallized from isopropyl ether to obtain 4.81 g of pure product melting at 112° C. and having a specific rotation of $[\alpha]_D = +52°$ ±1.5 (c=1% in CHCL$_3$).
Infra-red (CHCl$_3$):
1720 cm$^{-1}$: C=0,
1608, 1575, 1500 Cm$^{-1}$: aromatic.
Mass spectrum M+=338+.

EXAMPLE 2

A solution of 28.95 g of the product of Step A of Example 1 in 600 mg of tetrahydrofuran was added at −40° C. to −50° C. to 360 ml of condensed ammonia. 6 ml of ethanol were added, then 1.07 g of lithium were added in small pieces. After 15 to 20 minutes, 0.93 g of lithium and 6 ml of ethanol were added, then again two times 400 mg of lithium and 3 ml of ethanol were added. The ammonia was distilled off and the resultant mixture was diluted with water at ambient temperature. Extraction was carried out with ethyl acetate and the extracts were washed with water, dried and evaporated to obtain 29.6 g of reduction product which was treated with 285 ml of acetic acid with 25% water with stirring for one hour. 20 ml of ethyl ether were added and the mixture stood for three hours at ambient temperature. It was poured into dilute ammonium hydroxide, extracted with ethyl acetate and the extracts were washed with water, dried and evaporated. 29 g of the product were dissolved in 290 ml of pyridine and the solution was cooled down to 4° C. 29 g of pyridinium perbromide were added in fractions and the suspension was stirred at 4° C. for one hour, then left for 17 hours at ambient temperature. It was poured into ice-cooled water and extracted with methylene chloride. The organic phase was washed with dilute hydrochloric acid, then with water, dried and distilled to obtain 34 g of residue which was chromatographed on silica under pressure (eluant: cyclohexane - ethyl acetate (7-3)) to obtain 17 g of product which after crystallization from methanol yielded 16.42 g of the desired pure product melting at 192° C.

Infra-red (CHCl$_3$):

| 1722 cm$^{-1}$ | cyclopentanone |
| 866, 1609, 1659 cm$^{-1}$ | dienone |

Ultra-violet (Ethanol):
Maximum 303 nm epsilon=21700,
Inflexions 213, 228, 235, 246 nm,

EXAMPLE 3

Spiro (cyclopentane-1,17′β-Δ$^{4′,9′,11′}$-estratriene)-2,3′-dione

Spiro (cyclopentane-1,17′β-Δ$^{5′,(10′),9′(11′)}$-estradiene)-2,3′-dione cyclic 3′-(1,2-ethanediyl)-acetal 4 ml of ethyleneglycol and 2 g of pyridine hydrochloride were added to a solution of 9.46 g of the product of Example 2 in 190 ml of dry chloroform. The mixture was refluxed for 5 hours with stirring under nitrogen. After cooling, 2 ml of triethylamine were added and the mixture was diluted with an aqueous solution of sodium bicarbonate. The organic phase was decanted, washed with water, dried, filtered to obtain 13.4 g of crude product and the product was dissolved in a few ml of methylene chloride. The solution was diluted with ether and filtration was carried out over hyflosupercel, followed by diluting again with ethyl ether and concentrating. The suspension was ice-cooled and after separating, 8.145 g of the expected product melting at 129° C. were obtained by chromatographing the mother liquors after evaporation (eluant : cyclohexane - ethyl acetate (8-2)), another 1.48 g of the expected product were obtained.

Infra-red (CHCl$_3$):

| 1721 cm$^{-1}$ | cyclopentanone |
| 1641, 1616 cm$^{-1}$ | diene. |

STEP B: Spiro (cyclopentane-1,17′β-Δ$^{4′,9′,11′}$-estratriene)-2,3′-dione

A solution of 3.17 g of the product of Step A in 32 ml of acetic acid with 30% water was heated for one hour at 70° C. The solution was ice-cooled, diluted with water, and extracted with methylene chloride. The organic phase was washed with an aqueous solution of sodium bicarbonate, then with water. After drying and evaporating under reduced pressure, 2.88 g of product were treated in 30 ml of dioxane with 2.3 g of dichloro-dicyano-benzoquinone with stirring for 4 hours at ambient temperature. After diluting with an aqueous solution of 10% sodium thiosulfate, extraction was carried out with ethyl acetate. The extracts were washed with sodium bicarbonate and with water, then dried and distilled to obtain 2.97 g of resin which was purified by chromatography on silica (eluant: cyclohexane -ethyl acetate (8-2 then 7-3)) to obtain 2.075 g of pure product. An analytical sample was crystallized from a mixture of methylene chloride - isopropyl ether to obtain the desired product melting at 156° C.

Infra-red (CHCl$_3$):

| 1574–1649 cm$^{-1}$ | trienone |
| 1725 cm$^{-1}$ | cyclopentanone |

Ultra-violet (EtOH)
239 nm: maximum epsilon=6300;
340 nm: maximum epsilon=31200;
270 nm: inflexion.

EXAMPLE 4

(2S) 2-hydroxy-spiro (cyclopentane-1,17′β-Δ$^{4′,9′}$-estradien)-3′-one

STEP A: (2S) 3′-methoxy-spiro (cyclopentane-1,17′β-Δ$^{2′,5′(10′)}$-estra-dien)-2-ol-and corresponding (2R) isomer A solution of 2.04 g of 3′-methoxy-spiro (cyclopentane-1,17′β-Δ1′,3′,5′-estratrien)-2-one in 40 ml of tetrahydrofuran was added to a mixture of 400 mg of lithium in 100 ml of ammonia at −40° C. The flask was rinsed with 5 ml of tetrahydrofuran and 5 ml of tert-butyl alcohol. After 30 minutes of stirring at +40° C., the ammonia was distilled off. The mixture was diluted with an aqueous solution of ammonium chloride, then extracted with ethyl acetate. The organic phase was washed, dried and evaporated under reduced pressure to obtain 2.11 g of crude product which was chromatographed on silica (eluant: cyclohexane - ethyl acetate (8-2) and 1% triethylamine) to obtain 370 mg of 2R product and 1.375 g of 2S product. After crystallization of the 2S product from isopropyl ether, 132 mg of an analytical sample were obtained melting at 124° C.

Infra-red (CHCl$_3$):

| 2S Product | 2R Product |
|---|---|
| 3616 cm$^{-1}$: OH | 3616 cm$^{-1}$: OH |
| the C=C's: 1695–1664 cm$^{-1}$ | the C=C's: 1695–1665 cm$^{-1}$ |

STEP B: (2S) 2-hydroxy-spiro (cyclopentane-1,17′β-Δ$^{5′(10′)}$-estren)-3′-one 1 ml of ethyl ether was added to a solution of 200 mg of 2S product of Step A in 4 ml of 20% acetic acid and stood for 3 hours at ambient temperature. The reaction medium was diluted with water and extracted with methylene chloride. The extracts were washed with sodium bicarbonate, dried and evaporated under reduced pressure to obtain 190 mg of the expected product.
Infra-red (CHCl$_3$):
3614 cm$^{-1}$: OH
1714 cm$^{-1}$: 3-keto.

STEP C: (2S) 2-hydroxy-spiro (cyclopentane-1,17'$\beta$-$\Delta^{4',9'}$-estradien)-3'-one 200 mg of pyridinium perbromide were added to a solution of 185 mg of the product of Step B in 3 ml of pyridine and the mixture was stirred at ambient temperature for 15 hours. The mixture was diluted with water and extracted with methylene chloride. The organic phase was washed with 2N hydrochloric acid, then with water. After drying and evaporating under reduced pressure, 185 mg of the expected product were obtained. After chromatography on silica (eluant: cyclohexane - ethyl acetate (1-1)) and crystallization from isopropyl ether, 117 mg of the pure product melting at 187° C. were obtained.
Infra-red (CHCL$_3$):
3616 cm$^{-1}$: OH
1605-1652 cm$^{-1}$: dienone.
Ultra-violet (EtOH)
maximum 216 nm epsilon=6400,
maximum 304 nm epsilon=21600.

EXAMPLE 5

(2R) 2-hydroxy-spiro (cyclopentane-1,17'$\beta$-$\Delta^{4',9'}$-estradien)-3'-one Using the procedure of Step B of Example 4, 370 mg of 2R product of Step A of Example 4 were reacted to obtain 0.35 g of product which was dissolved in 15 ml of pyridine. 380 mg of pyridinium perbromide were added, the procedure of Step C of Example 4 was followed to obtain after crystallization from isopropyl ether 200 mg of the expected product melting at 210° C.
Infra-red (CHCl$_3$):
3612 cm$^{-1}$: OH,
1649-1605 cm$^{-1}$: dienone.
Ultra-violet:
Maximum 218 nm epsilon=6200,
Maximum 308 nm epsilon=21100.

EXAMPLE 6

Pharmaceutical Composition

Tablets were prepared containing 100 μg of the product of Example 2 and sufficient excipient of talc, starch and magnesium stearate for a final weight of 100 mg.

Pharmacological Study

Progestomimetic activity a) The progestomimetic activity of the products of Examples 1 and 2 was studied by the method of hormonal receptors described by RAYNAUD et al in "J. Ster. BIOCHEM" 1975, Vol. 6, 615 to 622 and in "Physiology and Genetics of Reproduction", 1975 part A p. 143 to 160. The technique was as follows: 25 mg of estradiol were administered to impuberal rabbits percutaneously. Five days after this treatment, the animals were killed, the uteri were removed and homogenized in a 10 mM tromethamine, 0.25 M saccharose, HCl pH 7.4 buffer. The homogenate was centrifuged at 105,000 g for one hour and the supernatant liquid or cytosol was adjusted to have a dilution of 1/50 (weight/volume). Tubes with the same volume of cytosol were incubated at 0° C. for two hours with a fixed concentration of tritiated 17,21-dimethyl-19-nor-$\Delta^{4,9}$-pregandiene-3,20-dione, called hereafter tritiated product R, in the presence or not of an increasing concentration of radio-inert 17,21-dimethyl-19-nor-$\Delta^{4,9}$-pregnadiene-3,20-dione called hereafter cold product R, of progesterone or of product under test. After two hours and after 24 hours, the radioactivity of bound tritiated product R was determined by the technique of absorption with cabon-dextran (1.25%-0.625%).

Then the following was traced: the straight line parallel to the axis of the abscesses, of the coordinate $$I_{50} = \frac{100\left(1 + \frac{Bmin}{Bo}\right)}{2}$$

Bo being the maximum quantity of bound tritiated product R, measured in the incubate containing only tritiated product R, Bmin being the minimum quantity of bound tritiated product R (non-specific), measured in the incubate containing tritiated product R plus a large excess of cold product R (2500 10$^{-9}$M), the curves representing the percentages of bound tritiated product $$R \frac{B}{Bo}$$

as a function of the logarithm of the concentrations of added cold product.

The intersections of the straight line I$_{50}$ and the curves allowed the values CP and CX to be determined. CP: concentration of cold progesterone which inhibited by 50% the fixing of the tritiated product R. CX: concentration of the product under test which inhibited by 50% the fixing of the tritiated product R.

The relative affinity of the product under test or RBA is given by the formula $$RBA = 100 \times \frac{CP}{CX}$$

Results:

|  | RBA 2 hours | RBA 24 hours |
|---|---|---|
| Progesterone | 100 | 100 |
| Product of Example 1 | 312 | 1012 |
| Product of Example 2 | 344 | 912 |

Conclusion: the products of Examples 1 and 2 have a very strong affinity for the specific receptor of progesterone.

b) The progestomimetic activity of the product of Example 2 was determined by the CLAUBERG test. According to this test, groups of three impuberal rabbits were sensitized before-hand by the administration of estradiol sub-cutaneously for five days at a daily dose of 5 micrograms. Two days later, they were treated daily for five days with the medicament under study sub-cutaneously. The animals were killed on the sixth day and the lacy proliferation of the endometrium on the uterine sections, which was characteristic of progestomimetic action, was noted in Mac Phail units.

The product of Example 2 was used in solution in sesame oil containing 5% benzyl alcohol.

| Compound | DOSES μg/rabbit/day | Mac Phail UNITS |
|---|---|---|
| Product of Example 2 | 0.3 | 0.5 |
| | 1 | 1.8 |
| | 3 | 2.8 |

2.8 Mac Phail units at a daily dose of 10 micrograms were thus obtained and the product therefore possesses a very strong progestomimetic activity.

Various modifications of the products and method of the invention may be made without departing from the spirit or scope thereof and it is to be understood that the invention is intended to be limited only as defined in the appended claims.

What we claim is:

1. Compounds of the formula

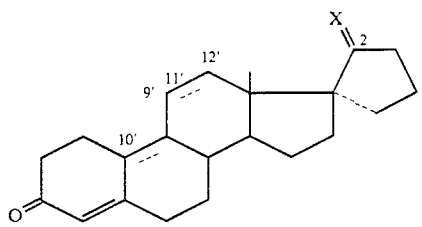  I wherein =X is =O or

,

R is hydrogen or acyl of an organic carboxylic acid of 1 to 12 carbon atoms, the wavy lines indicate the α- or β-position, the dotted line in the 17-position indicates the bond is in the α-position and the dotted lines in the 9'(10') and 11'(12') positions indicate an optional double bond in the 9'(10') position or two optional double bonds in the 9'(10') and 11'(12') positions.

2. A compound of claim 1 wherein =X is =O and there is no double bond in the 11'(12') position.

3. A compound of claim 1 which is spiro (cyclopentane-1,17'β-Δ$^{4',9'}$-estradiene)-2,3'-dione.

4. A compound having a formula selected from the group consisting of

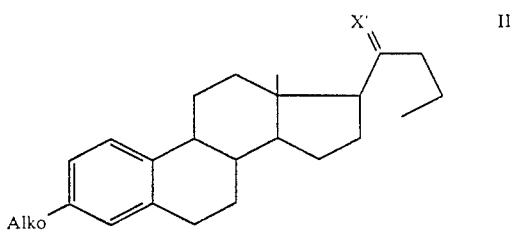 II and

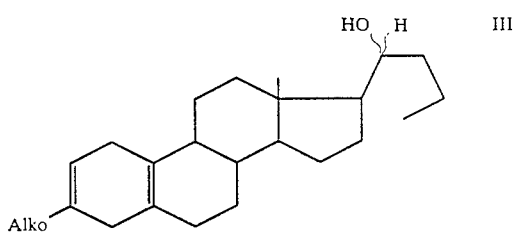 III wherein Alk is alkyl of 1 to 4 carbon atoms, =X' is optionally protected =O or

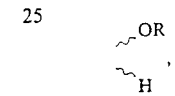,

R is hydrogen or acyl of an organic carboxylic acid of 1 to 12 carbon atoms, the wavy lines indicate the α- or β-position and the dotted line in the 17 -position indicates the α-position.

5. A progestomimetic composition comprising a progestomimetically effective amount of at least one compound of claim 1 and an inert pharmaceutical carrier.

6. A composition of claim 5 wherein =X is =O and there is no double bond in the 11'(12') position.

7. A composition of claim 5 wherein the active compound is spiro (cyclopentane-1,17'β-Δ$^{4',9'}$-estradiene)-2,3'-dione.

8. A method of inducing progestomimetic activity in warm-blooded animals comprising administering to warm-blooded animals a progestomimetically effective amount of at least one compound of claim 1.

9. A method of claim 8 wherein =X is =O and there is no double bond in the 11'(12') position.

10. A method of claim 8 wherein the active compound is spiro (cyclopentane-1,17'β-Δ$^{4',9'}$-estradiene)-2,3'-dione.

* * * * *

UNITED STATES PATENT AND TRADEMARK OFFICE
CERTIFICATE OF CORRECTION

PATENT NO. : 5,084,450

DATED : Jan. 28, 1992

INVENTOR(S) : Martine Gaillard-Kelly, et al.

It is certified that error appears in the above-identified patent and that said Letters Patent is hereby corrected as shown below:

Column 16, lines 1-21, claim 4, "

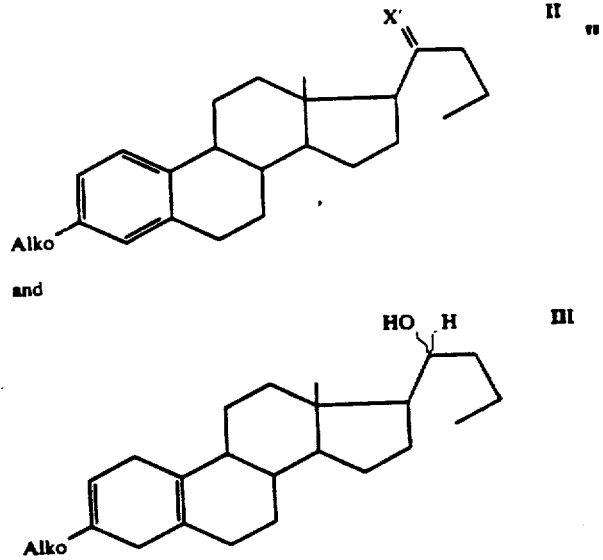

should read

UNITED STATES PATENT AND TRADEMARK OFFICE
CERTIFICATE OF CORRECTION

PATENT NO. : 5,084,450

DATED : Jan. 28, 1992

INVENTOR(S) : Martine Gaillard-Kelly, et al.

It is certified that error appears in the above-identified patent and that said Letters Patent is hereby corrected as shown below:

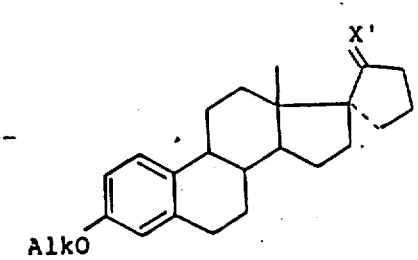 II and 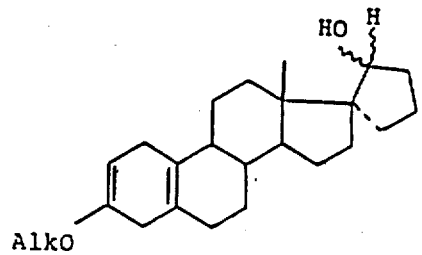 III

Signed and Sealed this

Twentieth Day of July, 1993

Attest:

MICHAEL K. KIRK

Attesting Officer     Acting Commissioner of Patents and Trademarks